US008519006B2

(12) United States Patent
Brinkmann et al.

(10) Patent No.: US 8,519,006 B2
(45) Date of Patent: Aug. 27, 2013

(54) USE OF SPHINGOSINE-1 PHOSPHATE (S1P) RECEPTOR AGONISTS FOR THE TREATMENT OF BRAIN DEGENERATIVE DISEASES

(75) Inventors: Volker Brinkmann, Freiburg (DE); Nicole Kaneider, Innsbruck (AT); Christian J Wiedermann, Innsbruck (AT)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/884,953

(22) Filed: Sep. 17, 2010

(65) Prior Publication Data

US 2011/0124739 A1 May 26, 2011

Related U.S. Application Data

(63) Continuation of application No. 10/583,106, filed as application No. PCT/EP2004/014436 on Dec. 17, 2004, now abandoned.

(30) Foreign Application Priority Data

Dec. 19, 2003 (GB) .................................. 0329498.0

(51) Int. Cl.
*A61K 31/137* (2006.01)
(52) U.S. Cl.
USPC .......................................... 514/653; 514/646
(58) Field of Classification Search
USPC ....................................................... 514/646
See application file for complete search history.

(56) References Cited

U.S. PATENT DOCUMENTS

| | | | | |
|---|---|---|---|---|
| 5,308,861 | A * | 5/1994 | Aizawa et al. | 514/410 |
| 6,004,565 | A | 12/1999 | Chiba et al. | |
| 6,277,888 | B1 * | 8/2001 | Sakai et al. | 514/653 |
| 6,420,369 | B1 | 7/2002 | Marcotte | |
| 6,960,692 | B2 | 11/2005 | Kohno et al. | |
| 6,963,012 | B2 | 11/2005 | Kohno et al. | |
| 2002/0102279 | A1 | 8/2002 | Chiba et al. | |
| 2007/0088002 | A1 | 4/2007 | Lynch et al. | |

FOREIGN PATENT DOCUMENTS

| | | |
|---|---|---|
| DE | 195 13 630 A1 | 10/1996 |
| EP | 0 627 406 | 10/1998 |
| EP | 0 778 263 | 1/2002 |
| EP | 1 002 792 | 7/2004 |
| JP | A-11-80026 | 3/1999 |
| JP | 2002 316985 | 10/2002 |
| WO | WO 96/25161 | 8/1996 |
| WO | WO 97/48391 | 12/1997 |
| WO | WO 98/20864 | 5/1998 |
| WO | WO00/50058 * | 8/2000 |
| WO | WO 01/74364 | 10/2001 |
| WO | WO 02/06268 | 1/2002 |
| WO | WO 02/18395 | 3/2002 |
| WO | WO 02/056892 | 7/2002 |
| WO | WO 02/076995 | 10/2002 |
| WO | WO 03/011269 | 2/2003 |
| WO | WO 03/047577 A2 | 6/2003 |
| WO | WO 03/061567 | 7/2003 |
| WO | WO 03/062252 | 7/2003 |
| WO | WO 03/029184 | 10/2003 |
| WO | WO 03/029205 | 10/2003 |
| WO | WO 03/094965 | 11/2003 |
| WO | WO 2004/010987 | 2/2004 |
| WO | WO 2004/024673 | 3/2004 |
| WO | WO 2004/026521 A2 | 4/2004 |
| WO | WO 2004/096752 | 11/2004 |
| WO | WO 2005/002559 | 1/2005 |
| WO | WO 2005/025553 | 3/2005 |

OTHER PUBLICATIONS

Gehrmann et al. Amyloid precursor protein (APP) expression in multiple sclerosis lesions. GLIA 15:141-151 (1995) Wiley-Liss, Inc.*
Extended European Search Report, dated Sep. 22, 2010.
Beers MH et al., "The Merck Manual of Diagnosis and Therapy, 17th Edition", Merck Research Laboratories, Whitehouse Station, NJ, pp. 1473-1476, (1999), [XP002582251].
Kaneider et al., "The Immune Modulator FTY720 Targets Sphingosine-Kinase-Dependent Migration of Human Monocytes in Response to Amyloid Beta-Protein and its Precursor", FASEB Journal, vol. 18, No. 11, pp. 1309-1311 (2004).
Masayuki, Fujino et al., "Amelioration of Experimental Autoimmune Encephalomyelitis in Lewis Rats by FTY720 Treatment", Journal of Pharmacology and Experimental Therapeutics, vol. 305,No. 1, pp. 70-77, (2003).
Keul et al.,"The Sphingosine-1-Phosphate Analogue FTY720 Reduces Atherosclerosis in Apolipoprtoein E-Feficient Mice", Arteriosclerosis, Thrombosis, and Vascular Biology, vol. 27, pp. 607-613, (2007).
Nofer et al., "FTY720, a Synthetic Sphingoosine 1 Phosphate Analogue, Inhibits Development of Atherosclerosis in Low-Density Lipoprtoein Receptor Deficient Mice", Circulation Journal of the American Hear Association, vol. 115, pp. 501-508, (2007).
Xie et al., "Sphingosine-1-phosphate receptor agonosim impairs the efficiency of the local immune response by battering trafficking of Naïve and antigen-activated CD4+ T cells", The Journal of Immunology, pp. 3362-3669, (Apr. 2003).
Quesniaux et al., "FTY-720 is efficacious in monkey kidney transplantation", Transplantation proceeding, 33, pp. 2774-2375 (2001).
Tokuda et al., Society for Neuroscience Abstracts, 2000, vol. 26, No. 1-2, Abstract No. 82.1.ISSN:0190-5295.
Watanabe, "Psychological effects of cyclosporine A", Immunosuppressant Analogs in neuroprotection, 2003, pp. 361-374, ISSN: 0-89603-944-7.
Casolaro Vincenzo et al "In vivo characterization of . . . " Journal of Immunology, vol. 151, No. 10, 1993, pp. 5563-5573, ISSN: 0022-1767.

* cited by examiner

*Primary Examiner* — Jennifer M Kim
(74) *Attorney, Agent, or Firm* — Karen DeBenedictis

(57) ABSTRACT

Disclosed is the use of sphingosine-1-phosphate (S1P) receptor agonists, preferably 2-amino-2-[2-(4-octylphenyl)ethyl]propane-1,3-diol, in the treatment of progressive dementia or brain degenerative diseases.

6 Claims, No Drawings

SEQUENCE LISTING

<160> NUMBER OF SEQ ID NOS: 10

<210> SEQ ID NO 1
<211> LENGTH: 18
<212> TYPE: DNA
<213> ORGANISM: artificial
<220> FEATURE:
<223> OTHER INFORMATION: Primer

<400> SEQUENCE: 1
ctgtgaacaa tgcactgg                                                       18

<210> SEQ ID NO 2
<211> LENGTH: 20
<212> TYPE: DNA
<213> ORGANISM: artificial
<220> FEATURE:
<223> OTHER INFORMATION: Primer

<400> SEQUENCE: 2
cctacgtact caacatagcc                                                     20

<210> SEQ ID NO 3
<211> LENGTH: 18
<212> TYPE: DNA

```
<213> ORGANISM: artificial
<220> FEATURE:
<223> OTHER INFORMATION: Primer

<400> SEQUENCE: 3
atctgcagct tcatcgtc                                                        18

<210> SEQ ID NO 4
<211> LENGTH: 15
<212> TYPE: DNA
<213> ORGANISM: artificial
<220> FEATURE:
<223> OTHER INFORMATION: Primer

<400> SEQUENCE: 4
agattgaggc agttc                                                           15

<210> SEQ ID NO 5
<211> LENGTH: 20
<212> TYPE: DNA
<213> ORGANISM: artificial
<220> FEATURE:
<223> OTHER INFORMATION: primer

<400> SEQUENCE: 5
accacgcaca gcacataatg                                                      20

<210> SEQ ID NO 6
<211> LENGTH: 20
<212> TYPE: DNA
<213> ORGANISM: artificial
<220> FEATURE:
<223> OTHER INFORMATION: Primer

<400> SEQUENCE: 6
aaacagcaag ttccactcgg                                                      20

<210> SEQ ID NO 7
<211> LENGTH: 18
<212> TYPE: DNA
<213> ORGANISM: artificial
<220> FEATURE:
<223> OTHER INFORMATION: primer

<400> SEQUENCE: 7
tgaacatcac gctgagtg                                                        18

<210> SEQ ID NO 8
<211> LENGTH: 18
<212> TYPE: DNA
<213> ORGANISM: artificial
<220> FEATURE:
<223> OTHER INFORMATION: primer

<400> SEQUENCE: 8
atcatcagca ccgtcttc                                                        18

<210> SEQ ID NO 9
<211> LENGTH: 18
<212> TYPE: DNA
<213> ORGANISM: artificial
<220> FEATURE:
<223> OTHER INFORMATION: primer

<400> SEQUENCE: 9
gaaatgcagc caaaggtg                                                        18
```

```
<210> SEQ ID NO 10
<211> LENGTH: 21
<212> TYPE: DNA
<213> ORGANISM: artificial
<220> FEATURE:
<223> OTHER INFORMATION: Primer

<400> SEQUENCE: 10
ttatcaccca caaggtcctt c                                           21
```

USE OF SPHINGOSINE-1 PHOSPHATE (S1P) RECEPTOR AGONISTS FOR THE TREATMENT OF BRAIN DEGENERATIVE DISEASES

This application is a continuation of application Ser. No. 10/583,106 which is a 371 of application No. PCT/EP2004/014436 filed on Dec. 17, 2004 which claims benefit of Great Britain Application No. 0329498.0 filed on Dec. 19, 2003, the entire disclosures of which are hereby incorporated by reference.

The present invention relates to a new use for a sphingosine-1-phosphate (S1P) receptor agonist, particularly in the treatment of progressive dementia or brain degenerative diseases.

S1P receptor agonists are compounds which signal as agonists at one or more sphingosine-1 phosphate receptors, e.g. S1P1 to S1P8. Agonist binding to a S1P receptor may e.g. result in dissociation of intracellular heterotrimeric G-proteins into Gα-GTP and Gβγ-GTP, and/or increased phosphorylation of the agonist-occupied receptor and activation of downstream signaling pathways/kinases, or to internalization/desensitization of the receptors as a result of super-agonism and consequently an antagonism of receptor signaling by the natural ligand S1P.

The binding affinity of S1P receptor agonists to individual human S1P receptors may be determined in following assay:

S1P receptor agonist activities of compounds are tested on the human S1P receptors $S1P_1$, $S1P_3$, $S1P_2$, $S1P_4$ and $S1P_5$. Functional receptor activation is assessed by quantifying compound induced GTP [$\gamma$-$^{35}$S] binding to membrane protein prepared from transfected CHO or RH7777 cells stably expressing the appropriate human S1P receptor. The assay technology used is SPA (scintillation proximity based assay). Briefly, DMSO dissolved compounds are serially diluted and added to SPA-bead (Amersham-Pharmacia) immobilised S1P receptor expressing membrane protein (10-20 µg/well) in the presence of 50 mM Hepes, 100 mM NaCl, 10 mM $MgCl_2$, 10 µM GDP, 0.1% fat free BSA and 0.2 nM GTP [$\gamma$-$^{35}$S] (1200 Ci/mmol). After incubation in 96 well microtiterplates at RT for 120 min, unbound GTP [$\gamma$-$^{35}$S] is separated by a centrifugation step. Luminescence of SPA beads triggered by membrane bound GTP [$\gamma$-$^{35}$S] is quantified with a TOPcount plate reader (Packard). $EC_{50}$s are calculated using standard curve fitting software. In this assay, the S1P receptor agonists preferably have a binding affinity to S1P receptor <50 nM.

Internalization and desensitization of S1P receptors is determined using e.g. Chinese hamster ovary (CHO) cells transfected with a myc-tagged human S1P receptor. Internationalization of the receptor as a results of stimulation by agonists is determined by FACS analysis using fluorescently labeled anti-myc antibodies.

Preferred S1P receptor agonists are e.g. compounds which in addition to their S1P binding properties also have accelerating lymphocyte homing properties, e.g. compounds which elicit a lymphopenia resulting from a re-distribution, preferably reversible, of lymphocytes from circulation to secondary lymphatic tissue, without evoking a generalized immunosuppression. Naïve cells are sequestered; CD4 and CD8 T-cells and B-cells from the blood are stimulated to migrate into lymph nodes (LN) and Peyer's patches (PP).

The lymphocyte homing property may be measured in following Blood Lymphocyte Depletion assay:

A S1P receptor agonist or the vehicle is administered orally by gavage to rats. Tail blood for hematological monitoring is obtained on day −1 to give the baseline individual values, and at 2, 6, 24, 48 and 72 hours after application. In this assay, the S1P receptor agonist depletes peripheral blood lymphocytes, e.g. by 50%, when administered at a dose of e.g. <20 mg/kg.

Preferred S1P receptor agonists are further compounds which in addition to their S1P binding properties internalize/desensitize S1P receptors, thereby antagonizing inflammatory processes driven by lysophospholipids, including i.e. sphingosine 1-phosphate (S1P), sphingophosphorylcholine (SPC), lysophosphatidic acid (LPA), and others, on vasculature cells, e.g. endothelial cells. The internalization/desensitization capacity of compounds will be determined using CHO cells transfected with a human myc-tagged SIP receptor.

Examples of appropriate S1P receptor agonists are, for example:

Compounds as disclosed in EP627406A1, e.g. a compound of formula I

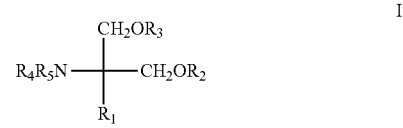

wherein $R_1$ is a straight- or branched $(C_{12-22})_{carbon}$ chain
  which may have in the chain a bond or a hetero atom selected from a double bond, a triple bond, O, S, $NR_6$, wherein $R_6$ is H, alkyl, aralkyl, acyl or alkoxycarbonyl, and carbonyl, and/or
  which may have as a substituent alkoxy, alkenyloxy, alkynyloxy, aralkyloxy, acyl, alkylamino, alkylthio, acylamino, alkoxycarbonyl, alkoxycarbonylamino, acyloxy, alkylcarbamoyl, nitro, halogen, amino, hydroxyimino, hydroxy or carboxy; or $R_1$ is
  a phenylalkyl wherein alkyl is a straight- or branched $(C_{6-20})$carbon chain; or
  a phenylalkyl wherein alkyl is a straight- or branched $(C_{1-30})$carbon chain wherein said phenylalkyl is substituted by
    a straight- or branched $(C_{6-20})$carbon chain optionally substituted by halogen,
    a straight- or branched $(C_{6-20})$alkoxy chain optionally substituted by halogen,
    a straight- or branched $(C_{6-20})$alkenyloxy,
    phenylalkoxy, halophenylalkoxy, phenylalkoxyalkyl, phenoxyalkoxy or phenoxyalkyl,
    cycloalkylalkyl substituted by $C_{6-20}$alkyl,
    heteroarylalkyl substituted by $C_{6-20}$alkyl,
    heterocyclic $C_{6-20}$alkyl or
    heterocyclic alkyl substituted by $C_{2-20}$alkyl,
and wherein
the alkyl moiety may have
  in the carbon chain, a bond or a heteroatom selected from a double bond, a triple bond, O, S, sulfinyl, sulfonyl, or $NR_6$, wherein $R_6$ is as defined above, and
  as a substituent alkoxy, alkenyloxy, alkynyloxy, aralkyloxy, acyl, alkylamino, alkylthio, acylamino, alkoxycarbonyl, alkoxycarbonylamino, acyloxy, alkylcarbamoyl, nitro, halogen, amino, hydroxy or carboxy, and
each of $R_2$, $R_3$, $R_4$ and $R_5$, independently, is H, $C_{1-4}$ alkyl or acyl
or a pharmaceutically acceptable salt thereof;

Compounds as disclosed in EP 1002792A1, e.g. a compound of formula II

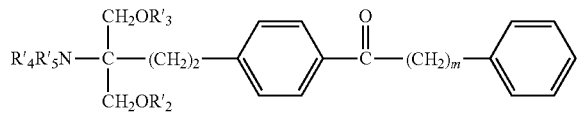

wherein m is 1 to 9 and each of $R'_2$, $R'_4$ and $R'_5$, independently, is H, alkyl or acyl,
or a pharmaceutically acceptable salt thereof;

Compounds as disclosed in EP0778263 A1, e.g. a compound of formula III

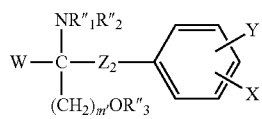

wherein W is H; $C_{1-6}$alkyl, $C_{2-6}$alkenyl or $C_{2-6}$alkynyl; unsubstituted or by OH substituted phenyl; $R''_4$—O—$(CH_2)_n$; or $C_{1-6}$alkyl substituted by 1 to 3 substituents selected from the group consisting of halogen, $C_{3-6}$cycloalkyl, phenyl and phenyl substituted by OH;
X is H or unsubstituted or substituted straight chain alkyl having a number p of carbon atoms or unsubstituted or substituted straight chain alkoxy having a number (p-1) of carbon atoms, e.g. substituted by 1 to 3 substitutents selected from the group consisting of $C_{1-6}$ alkyl, OH, $C_{1-6}$alkoxy, acyloxy, amino, $C_{1-6}$alkylamino, acylamino, oxo, halo$C_{1-6}$alkyl, halogen, unsubstituted phenyl and phenyl substituted by 1 to 3 substituents selected from the group consisting of $C_{1-6}$alkyl, OH, $C_{1-9}$alkoxy, acyl, acyloxy, amino, $C_{1-6}$alkylamino, acylamino, halo$C_{1-6}$alkyl and halogen; Y is H, $C_{1-6}$alkyl, OH, $C_{1-6}$alkoxy, acyl, acyloxy, amino, $C_{1-6}$alkylamino, acylamino, halo$C_{1-6}$alkyl or halogen, $Z_2$ is a single bond or a straight chain alkylene having a number or carbon atoms of q, each of p and q, independently, is an integer of 1 to 20, with the proviso of $65 \leq p+q \leq 23$, m' is 1, 2 or 3, n is 2 or 3,
each of $R''_2$, $R''_2$, $R''_3$ and $R''_4$, independently, is H, $C_{1-4}$alkyl or acyl,
or a pharmaceutically acceptable salt thereof, Compounds as disclosed in WO02/18395, e.g. a compound of formula IVa or IVb

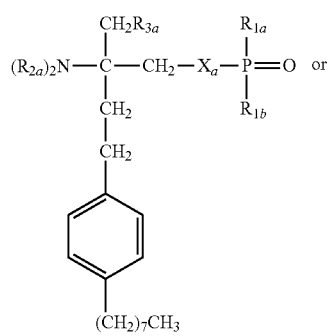

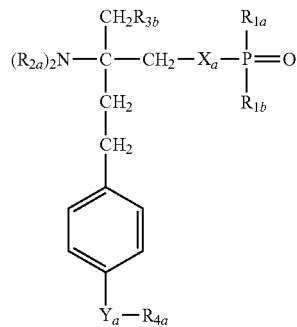

wherein $X_a$ is O, S, $NR_{1s}$ or a group —$(CH_2)_{na}$—, which group is unsubstituted or substituted by 1 to 4 halogen; $n_a$ is 1 or 2, $R_{1s}$ is H or $(C_{1-4})$alkyl, which alkyl is unsubstituted or substituted by halogen; $R_{1a}$ is H, OH, $(C_{1-4})$alkyl or $O(C_{1-4})$alkyl wherein alkyl is unsubstituted or substituted by 1 to 3 halogen; $R_{1b}$ is H, OH or $(C_{1-4})$alkyl, wherein alkyl is unsubstituted or substituted by halogen; each $R_{2a}$ is independently selected from H or $(C_{1-4})$alkyl, which alkyl is unsubstituted or substituted by halogen; $R_{1a}$ is H, OH, halogen or $O(C_{1-4})$alkyl wherein alkyl is unsubstituted or substituted by halogen; and $R_{3b}$ is H, OH, halogen, $(C_{1-4})$alkyl wherein alkyl is unsubstituted or substituted by hydroxy, or $O(C_{1-4})$alkyl wherein alkyl is unsubstituted or substituted by halogen; $Y_a$ is —$CH_2$—, —O(O)—, —CH(OH)—, —C(=NOH)—, O or S, and $R_{4a}$ is $(C_{4-14})$alkyl or $(C_{4-14})$alkenyl;
or a pharmaceutically acceptable salt or hydrate thereof;

Compounds as disclosed in WO 02/076995, e.g. a compound of formula V

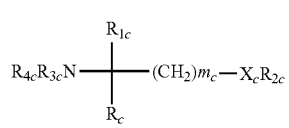

wherein
$m_c$ is 1, 2 or 3;
$X_c$ is 0 or a direct bond;
$R_{1c}$ is H; $C_{1-8}$ alkyl optionally substituted by OH, acyl, halogen, $C_{3-10}$cycloalkyl, phenyl or hydroxy-phenylene; $C_{2-6}$alkenyl; $C_{2-6}$alkynyl; or phenyl optionally substituted by OH;
$R_{2c}$ is

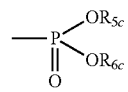

wherein $R_{5c}$ is H or $C_{1-4}$alkyl optionally substituted by 1, 2 or 3 halogen atoms, and $R_{6c}$ is H or $C_{1-4}$alkyl optionally substituted by halogen;
each of $R_{3c}$ and $R_{4c}$, independently, is H, $C_{1-4}$alkyl optionally substituted by halogen, or acyl, and
$R_c$ is $C_{13-20}$alkyl which may optionally have in the chain an oxygen atom and which may optionally be substituted by nitro, halogen, amino, hydroxy or carboxy; or a residue of formula (a)

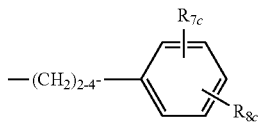

(a)

wherein $R_{7c}$ is H, $C_{1-4}$alkyl or $C_{1-4}$alkoxy, and $R_{8c}$ is substituted $C_{1-20}$alkanoyl, phenyl$C_{1-14}$alkyl wherein the $C_{1-14}$alkyl is optionally substituted by halogen or OH, cycloalkyl$C_{1-14}$alkoxy or phenyl$C_{1-14}$alkyl wherein the cycloalkyl or phenyl ring is optionally substituted by halogen, $C_{1-4}$alkyl and/or $C_{1-4}$alkoxy, phenyl $C_{1-14}$alkoxy-$C_{1-14}$alkyl, phenoxy$C_{1-14}$alkoxy or phenoxy$C_{1-14}$alkyl, $R_c$ being also a residue of formula (a) wherein $R_{8c}$ is $C_{1-14}$alkoxy when $R_{1c}$ is $C_{1-4}$alkyl, $C_{2-6}$alkenyl or $C_{2-6}$alkynyl, or a compound of formula VI

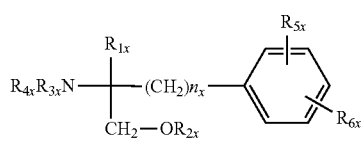

VI wherein $n_x$ is 2, 3 or 4

$R_{1x}$ is H; $C_{1-6}$alkyl optionally substituted by OH, acyl, halogen, cycloalkyl, phenyl or hydroxy-phenylene; $C_{2-6}$alkenyl; $C_{2-6}$alkynyl; or phenyl optionally substituted by OH;

$R_{1x}$ is H, $C_{1-4}$ alkyl or acyl each of $R_{3x}$ and $R_{4x}$, independently is H, $C_{1-4}$alkyl optionally substituted by halogen or acyl, $R_{5x}$ is H, $C_{1-4}$alkyl or $C_{1-4}$alkoxy, and $R_{6x}$ is $C_{1-20}$ alkanoyl substituted by cycloalkyl; cyloalkyl$C_{1-14}$alkoxy wherein the cycloalkyl ring is optionally substituted by halogen, $C_{1-4}$alkyl and/or $C_{1-4}$alkoxy; phenyl$C_{1-4}$alkoxy wherein the phenyl ring is optionally substituted by halogen, $C_{1-4}$alkyl and/or $C_{1-4}$alkoxy, $R_{6x}$ being also $C_{4-14}$alkoxy when $R_{1x}$ is $C_{2-4}$alkyl substituted by OH, or pentyloxy or hexyloxy when $R_{1x}$ is $C_{1-4}$alkyl, provided that $R_{6x}$ is other than phenyl-butylenoxy when either $R_{5x}$ is H or $R_{1x}$ is methyl, or a pharmaceutically acceptable salt thereof;

Compounds as disclosed in WO02/06268A1, e.g. a compound of formula VII

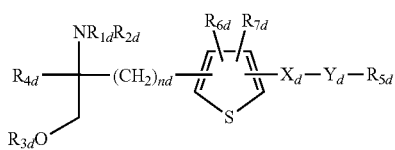

VII wherein each of $R_{1d}$ and $R_{2d}$, independently, is H or an amino-protecting group;

$R_{3d}$ is hydrogen, a hydroxy-protecting group or a residue of formula

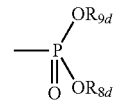

$R_{4d}$ is lower alkyl;

$n_d$ is an integer of 1 to 6;

$X_d$ is ethylene, vinylene, ethynylene, a group having a formula -D—CH$_2$— (wherein D is carbonyl, —CH(OH)—, O, S or N), aryl or aryl substituted by up to three substitutents selected from group a as defined hereinafter;

$Y_d$ is single bond, $C_{1-10}$alkylene, $C_{1-10}$alkylene which is substituted by up to three substitutents selected from groups a and b, $C_{1-10}$alkylene having O or S in the middle or end of the carbon chain, or $C_{1-10}$alkylene having O or S in the middle or end of the carbon chain which is substituted by up to three substituents selected from groups a and b;

$R_{5d}$ is hydrogen, cycloalkyl, aryl, heterocycle, cycloalkyl substituted by up to three substituents selected from groups a and b, aryl substituted by up to three substituents selected from groups a and b, or heterocycle substituted by up to three substituents selected from groups a and b;

each of $R_{6d}$ and $R_{7d}$, independently, is H or a substituent selected from group a;

each of $R_{8d}$ and $R_{9d}$, independently, is H or $C_{1-4}$alkyl optionally substituted by halogen;

<group a> is halogen, lower alkyl, halogeno lower alkyl, lower alkoxy, lower alkylthio, carboxyl, lower alkoxycarbonyl, hydroxy, lower aliphatic acyl, amino, mono-lower alkylamino, di-lower alkylamino, lower aliphatic acylamino, cyano or nitro; and <group b> is cycloalkyl, aryl, heterocycle, each being optionally substituted by up to three substituents selected from group a;

with the proviso that when $R_{5d}$ is hydrogen, $Y_d$ is a either a single bond or linear $C_{1-10}$ alkylene, or a pharmacologically acceptable salt or ester thereof;

Compounds as disclosed in JP-14316985 (JP2002316985), e.g. a compound of formula VIII:

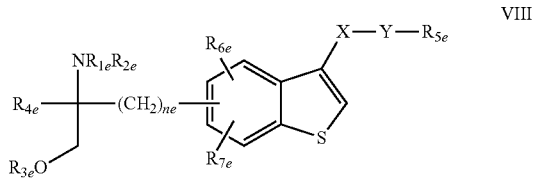

VIII wherein $R_{1e}$, $R_{2e}$, $R_{3e}$, $R_{4e}$, $R_{5e}$, $R_{6e}$, $R_{7e}$, $n_e$, $X_e$ and $Y_e$ are as disclosed in JP-14316985;

or a pharmacologically acceptable salt or ester thereof;

Compounds as disclosed in WO 03/29184 and WO 03/29205, e.g. compounds of formula IX

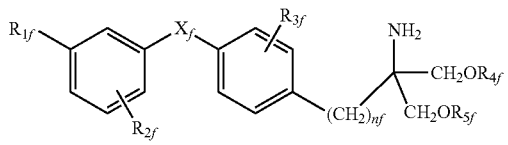

IX wherein $X_f$ is O or S, and $R_{1f}$, $R_{2f}$, $R_{3f}$ and $n_f$ are as disclosed in WO 03/29184 and 03/29205, each of $R_{4f}$ and $R_{5f}$ independently is H or a residue of formula

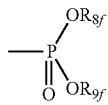

wherein each of $R_{8f}$ and $R_{9f}$, independently, is H or $C_{1-4}$alkyl optionally substituted by halogen; e.g. 2-amino-2-[4-(3-benzyloxyphenoxy)-2-chlorophenyl]propyl-1,3-propane-diol or 2-amino-2-[4-(benzyloxyphenylthio)-2-chlorophenyl]propyl-1,3-propane-diol, or a pharmacological salt thereof;

Compounds as disclosed in WO03/062252A1, e.g. a compound of formula X

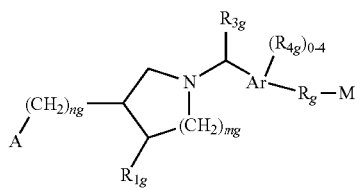

wherein
Ar is phenyl or naphthyl; each of $m_g$ and $n_g$ independently is 0 or 1; A is selected from COOH, $PO_3H_2$, $PO_2H$ $SO_3H$ $PO(C_{1-3}alkyl)OH$ and 1H-tetrazol-5-yl; each of $R_{1g}$ and $R_{2g}$ independently is H, halogen, OH, COOH or $C_{1-4}$alkyl optionally substituted by halogen; $R_{3g}$ is H or $C_{1-4}$alkyl optionally substituted by halogen or OH; each $R_{4g}$ independently is halogen, or optionally halogen substituted $C_{1-4}$alkyl or $C_{1-3}$alkoxy; and each of $R_g$ and M has one of the significances as indicated for B and C, respectively, in WO03/062252A1;

Compounds as disclosed in WO 03/062248A2, e.g. a compound of formula XI

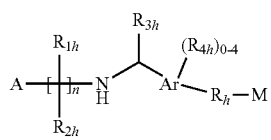

wherein Ar is phenyl or naphthyl; n is 2, 3 or 4; A is COOH, 1H-tetrazol-5-yl, $PO_3H_2$, $PO_2H_2$, —$SO_3H$ or $PO(R_{5h})OH$ wherein $R_{5h}$ is selected from $C_{1-4}$alkyl, hydroxy$C_{1-4}$alkyl, phenyl, —CO—$C_{1-3}$alkoxy and —CH(OH)-phenyl wherein said phenyl or phenyl moiety is optionally substituted; each of $R_{1h}$ and $R_{2h}$ independently is H, halogen, OH, COOH, or optionally halogeno substituted $C_{1-6}$alkyl or phenyl; $R_{3h}$ is H or $C_{1-4}$alkyl optionally substituted by halogen and/OH; each $R_{4h}$ independently is halogeno, OH, COOH, $C_{1-4}$alkyl, $S(O)_{0,1 \text{ or } 2}$ $C_{1-3}$alkyl, $C_{1-3}$alkoxy, $C_{3-6}$cycloalkoxy, aryl or aralkoxy, wherein the alkyl portions may optionally be substituted by 1-3 halogens; and each of $R_g$ and M has one of the significances as indicated for B and C, respectively, in WO03/062248A2;

Compounds as disclosed in WO 04/026817, e.g. a compound of formula XII

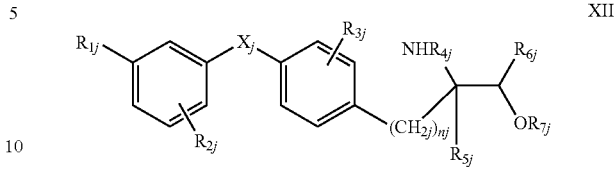

wherein $R_{1j}$ is halogen, trihalomethyl, $C_{1-4}$alkyl, $C_{1-4}$alkoxy, $C_{1-4}$alkylthio, aralkyl, or optionally substituted phenoxy or aralkyloxy, $R_{2j}$ is H, halogen, trihalomethyl, $C_{1-4}$alkyl, $C_{1-4}$alkoxy, aralkyl or aralkyloxy, $R_{3j}$ is H, halogen, trifluoromethyl, $C_{1-4}$alkyl, $C_{1-4}$alkoxy, $C_{1-4}$alkylthio or benzyloxy, $R_{4j}$ is H, $C_{1-4}$alkyl, phenyl, benzyl optionally substituted, lower aliphatic acyl having 1 to 5 C or benzoyl optionally substituted, $R_{5j}$ is H, monohalomethyl, $C_{1-4}$alkyl, $C_{1-4}$alkoxy, $C_{1-4}$alkylthio, hydroxyethyl, hydroxypropyl, phenyl, aralkyl, $C_{2-4}$alkenyl or $C_{2-4}$alkynyl, each of $R_{6j}$ and $R_{7j}$, independently is H or $C_{1-4}$alkyl, $X_j$ is O, S, SO or $SO_2$ and $n_j$ is 1, 2, 3 or 4, or a pharmaceutically acceptable salt thereof;

According to a further embodiment of the invention, a S1P receptor agonist for use in a combination of the invention may also be a selective S1P1 receptor, e.g. a compound which possesses a selectivity for the S1P1 receptor over the S1P3 receptor of at least 20 fold, e.g. 100, 500, 1000 or 2000 fold, as measured by the ratio of $EC_{50}$ for the S1P1 receptor to the $EC_{50}$ for the S1P3 receptor as evaluated in a $^{35}$S-GTPγS binding assay, said compound having an $EC_{50}$ for binding to the S1P1 receptor of 100 nM or less as evaluated by the $^{35}$S-GTPγS binding assay. Representative S1P1 receptor agonists are e.g. the compounds listed in WO 03/061567, the contents of which being incorporated herein by reference, for instance a compound of formula

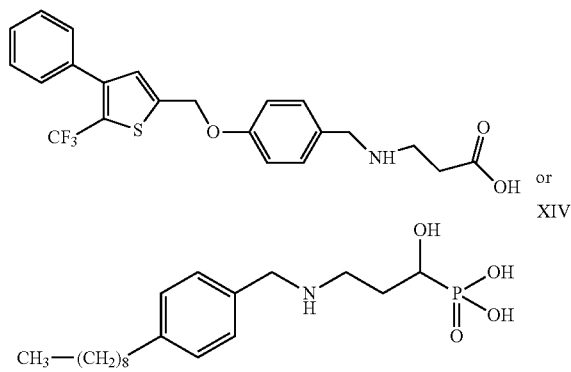

When the compounds of formulae I to XIV have one or more asymmetric centers in the molecule, the present invention is to be understood as embracing the various optical isomers, as well as racemates, diastereoisomers and mixtures thereof are embraced. Compounds of formula III or IVb, when the carbon atom bearing the amino group is asymmetric, have preferably the R-configuration at this carbon atom.

The compounds of formulae I to XIV may exist in free or salt form. Examples of pharmaceutically acceptable salts of the compounds of the formulae I to XIII include salts with inorganic acids, such as hydrochloride, hydrobromide and sulfate, salts with organic acids, such as acetate, fumarate, maleate, benzoate, citrate, malate, methanesulfonate and benzenesulfonate salts, or, when appropriate, salts with metals such as sodium, potassium, calcium and aluminium, salts with amines, such as triethylamine and salts with dibasic amino acids, such as lysine. The compounds and salts of the combination of the present invention encompass hydrate and solvate forms.

In each case where citations of patent applications are given, the subject matter relating to the compounds is hereby incorporated into the present application by reference.

Acyl may be a residue $R_y$—CO— wherein $R_y$ is $C_{1-6}$alkyl, $C_{3-6}$cycloalkyl, phenyl or phenyl-$C_{1-4}$alkyl. Unless otherwise stated, alkyl, alkoxy, alkenyl or alkynyl may be straight or branched.

When in the compounds of formula I the carbon chain as $R_1$ is substituted, it is preferably substituted by halogen, nitro, amino, hydroxy or carboxy. When the carbon chain is interrupted by an optionally substituted phenylene, the carbon chain is preferably unsubstituted. When the phenylene moiety is substituted, it is preferably substituted by halogen, nitro, amino, methoxy, hydroxy or carboxy.

Preferred compounds of formula I are those wherein $R_1$ is $C_{13-20}$alkyl, optionally substituted by nitro, halogen, amino, hydroxy or carboxy, and, more preferably those wherein $R_1$ is phenylalkyl substituted by $C_{6-14}$-alkyl chain optionally substituted by halogen and the alkyl moiety is a $C_{1-6}$alkyl optionally substituted by hydroxy. More preferably, $R_1$ is phenyl-$C_{1-6}$alkyl substituted on the phenyl by a straight or branched, preferably straight, $C_{6-14}$alkyl chain. The $C_{6-14}$alkyl chain may be in ortho, meta or para, preferably in para.

Preferably each of $R_2$ to $R_5$ is H.

A preferred compound of formula I is 2-amino-2-tetradecyl-1,3-propanediol. A particularly preferred S1P receptor agonist of formula I is FTY720, i.e. 2-amino-2-[2-(4-octylphenyl)ethyl]propane-1,3-diol in free form or in a pharmaceutically acceptable salt form (referred to hereinafter as Compound A), e.g. the hydrochloride, as shown:

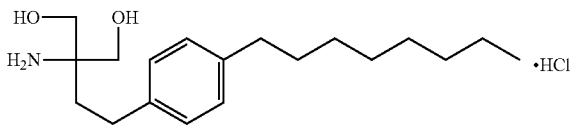 [SMILES: CCCCCCCCc1ccc(CCC(N)(CO)CO)cc1 ; Cl]

A preferred compound of formula II is the one wherein each of $R'_2$ to $R'_5$ is H and m is 4, i.e. 2-amino-2-{2-[4-(1-oxo-5-phenylpentyl)phenyl]ethyl}propane-1,3-diol, in free form or in pharmaceutically acceptable salt form (referred to hereinafter as Compound B), e.g the hydrochloride.

A preferred compound of formula III is the one wherein W is $CH_3$, each of $R''_1$ to $R''_3$ is H, $Z_2$ is ethylene, X is heptyloxy and Y is H, i.e. 2-amino-4-(4-heptyloxyphenyl)-2-methylbutanol, in free form or in pharmaceutically acceptable salt form (referred to hereinafter as Compound C), e.g. the hydrochloride. The R-enantiomer is particularly preferred.

A preferred compound of formula IVa is the FTY720-phosphate ($R_{2a}$ is H, $R_{3a}$ is OH, $X_a$ is O, $R_{1a}$ and $R_{1b}$ are OH). A preferred compound of formula IVb is the Compound C-phosphate ($R_{2a}$ is H, $R_{3b}$ is OH, $X_a$ is O, $R_{1a}$ and $R_{1b}$ are OH, $Y_a$ is O and $R_{4a}$ is heptyl). A preferred compound of formula V is Compound B-phosphate.

A preferred compound of formula V is phosphoric acid mono-[(R)-2-amino-2-methyl-4-(4-pentyloxy-phenyl)-butyl]ester.

A preferred compound of formula VIII is (2R)-2-amino-4-[3-(4-cyclohexyloxybutyl)-benzo[b]thien-6-yl]-2-methylbutan-1-ol.

Preferred compounds of formula XII are those wherein $R_{1j}$ is $CF_3$ or benzyloxy and $R_{6j}$ is H Compounds of formulae I to XIV have, on the basis of observed activity, e.g. as described in EP-A1-627,406, been found to be useful e.g. as immunosuppressants, e.g. in the treatment of acute allograft rejection or autoimmune disorders.

Brain degenerative diseases are becoming more common in developed nations as the population includes more and more older persons. There is no known cause for the diseases. It is not known why some people present as early as 30 or 40 years of age with dementia while others do not present until their late 70's or 80's. Alzheimer disease is a progressive degenerative disease of the brain characterized by the insidious onset of dementia. Impairment of memory, judgment, attention span, and problem solving skills are followed by global loss of cognitive abilities. There remains a medical need for agents which are effective in the treatment of such diseases and disorders, e.g. in reducing or preventing disease progression and/or alleviating the symptoms and/or improving quality of life. It has now been found that S1P receptor agonists have interesting properties which make them useful for treating progressive dementia and brain degeneration.

In accordance with the particular findings of the present invention, there is provided:

1.1 A method for treating progressive dementia or brain degeneration in a subject in need thereof, comprising administering to said subject a therapeutically effective amount of a sphingosine-1-phosphate (S1P) receptor agonist, e.g. a compound of formula I or a pharmaceutically acceptable salt thereof.

1.2 A method for treating β-amyloid-related inflammatory diseases or disorders in a subject in need thereof, comprising administering to said subject a therapeutically effective amount of a sphingosine-1-phosphate (S1P) receptor agonist, e.g. a compound of formula I or a pharmaceutically acceptable salt thereof.

Examples of such diseases and disorders are e.g. Alzheimer disease, amyloidosis, Lewy Body diseases, Multi-Infarct dementia, Pick's disease or cerebral atherosclerosis.

1.3 A method for reducing or inhibiting loss of cognitive abilities in a subject in need thereof, comprising administering to said subject a therapeutically effective amount of a sphingosine-1-phosphate (S1P) receptor agonist, e.g. a compound of formula I or a pharmaceutically acceptable salt thereof.

2. A sphingosine-1-phosphate (S1P) receptor agonist, e.g. a compound of formula I, or a pharmaceutically acceptable salt thereof for use in the preparation of a pharmaceutical composition for use in any method as defined under 1.1 to 1.3 above.

3. A pharmaceutical composition for use in any method as defined under 1.1 to 1.3 above comprising a sphingosine-1-phosphate (S1P) receptor agonist, e.g. a compound of formula I or a pharmaceutically acceptable salt thereof together with one or more pharmaceutically acceptable diluents or carriers therefor.

Preferably the progressive dementia or brain degeneration is other than senile dementia.

Utility of the sphingosine-1-phosphate (S1P) receptor agonists, e.g. a compound of formula I, in treating diseases as hereinabove specified, may be demonstrated in animal test methods as well as in clinic, for example in accordance with the methods hereinafter described.

A.1 Peripheral blood mononuclear cells are prepared from peripheral venous blood of healthy volunteers (anticoagulated with EDTA). After Lymphoprep$^R$ density gradient centrifugation, peripheral blood mononuclear cells are collected and washed three times with normal saline. Positive selection of monocytes is performed by adding MACS colloidal superparamagnetic microbeads conjugated with monoclonal anti-human CD14 antibodies to cooled, freshly prepared peripheral blood mononuclear cell preparations in MACS buffer (PBS with 5 mM EDTA and 0.5% bovine serum albumin) according to the manufacturer's instructions. Cells and microbeads are incubated for 15 min at 4-6° C. In the meantime the separation column is positioned in the MACS magnetic field and washed with MACS buffer at room temperature. The cells are washed with MACS buffer, resuspended, and loaded onto the top of the separation column. The eluent containing CD14$^-$ cells is withdrawn and after removal of the column from the magnet, trapped monocytes (CD14$^+$) are eluted with the sixfold amount of cold MACS buffer, centrifuged, and resuspended in medium containing 0.5% BSA. By immunocytochemistry, preparations yield a purity of approximately 98%.

Chemotaxis Assay

Leukocyte migration is measured using a modified 48-blindwell microchemotaxis chamber equipped with 5 µm pore-sized nitrocellulose filters for monocyte chemotaxis. In some experiments cells are incubated for 20 min with GFX [500 nM], staurosporine [10 ng/mL], tyrphostin-23 [10 ng/mL], wortmannin [10 nM], cholera toxin [1 nM], DMS [20 pg/mL to 20 µg/mL] or pertussis toxin [1 nM]. For determination of Aβ's potency to affect monocyte chemotaxis toward fMLP, cells with Aβ [1 aM to 1 µM] are incubated for 20 min. After washing twice, 50 µl of cell suspension [1×10$^6$ cells/mL] is put into the upper compartment of the chemotaxis chamber and cells are allowed to migrate for 90 min toward fMLP. After these migration periods the filters are dehydrated, fixed and stained with haematoxylin-eosin. Migration depth is quantified by microscopy, the distance from the surface of the filter to the leading front of three cells being measured. Data are expressed as "chemotaxis index", which is the ratio between the distance of directed and undirected migration.

Semiquantitative RT-PCR

Total RNA is isolated from 8×10$^6$ cells by phenol-chloroform-isoamylalcohol extraction (RNAClean™; Hybaid-AGS, Ulm, Germany). Reverse transcriptase reaction is performed on 1 µg of RNA using random hexamers reverse transcriptase (Gibco BRL, Life Technologies, Vienna, Austria). 10 µL of the reverse transcriptase reaction mixture is then subjected to 35 cycles of PCR in a 50 µL reaction mixture containing 1 pmol of sense and anti-sense primer pairs in a Perkin-Elmer thermocycler: 95° C.—30 sec (denaturation), 53° C.—60 sec (annealing), 72° C.—30 sec (extension). Hot Start Taq polymerase is from Qiagen Inc. (Valencia, Calif., USA). Primers (MWG Biotech, Ebersdorf, Germany) are designed to amplify about 400 bp coding sequences of the receptors. Primers are designed as follows: Sphingosine-1-phosphate receptor (S1PR) 1 sense: CTG TGA ACA ATG CAC TGG (SEQ ID NO:1), anti-sense: CCT ACG TAC TCA ACA TAG CC (SEQ ID NO:2). S1 PR 3:sense: ATC TGC AGC TTC ATC GTC (SEQ ID NO:3, anti-sense: AGA TTG AGG CAG TTC (SEQ ID NO:4). S1PR 2 sense: ACC ACG CAC AGC ACA TAA TG (SEQ ID NO:5), anti-sense: AAA CAG CM GTT CCA CTC GG (SEQ ID NO:6). S1 PR 4 sense: TGA ACA TCA CGC TGA GTG (SEQ ID NO:7), anti-sense: ATC ATC AGC ACC GTC TTC SEQ ID NO:8). S1PR 5 sense: GM ATG CAG CCA MG GTG (SEQ ID, NO:91, anti-sense: TT ATC ACC CAC AAG GTC CTT C (SEQ ID NO:10). The PCR products are subjected to agarose gel analysis.

Results

Aβ- and Aβ Precursor Protein-Induced Chemotaxis.

To confirm that Aβ induces monocyte chemotaxis and to investigate whether Aβ precursor protein (Aβ-PP) is able to act comparably, monocytes are allowed to migrate toward different concentrations of Aβ [10 nmol/L to 1 µmol/L] or Aβ-PP [10 nmol/L to 1 µmol/L] for 90 min. Directed migration of monocytes is measured using a modified 48-blindwell microchemotaxis chamber equipped with 5 µm pore-sized nitrocellulose filters for monocyte chemotaxis. Migration depth is quantified by microscopy, measuring the distance from the surface of the filter to the leading front of three cells. Data are expressed as "chemotaxis index", which is the ratio between the distance of directed and undirected migration. Mean distance of undirected migration was 57±4.5 µm. Results confirm that Aβ induces chemotaxis in human monocytes with a maximum response at 1 pmol/L. Aβ-PP induces chemotaxis in a concentration-dependent manner, with the maximal response also at 1 pM.

Inhibition of Aβ and Aβ-Precursor Protein-Induced Monocyte Migration by Neuropeptides.

To delineate whether monocyte attracting neuropeptides influence Aβ- and Aβ-PP-induced monocyte locomotion, cells are exposed to neuropeptides, e.g. bombesin, CGRP, SP, SN or VIP and chemotaxis toward Aβ and Aβ-PP is tested as described above. All neuropeptides inhibit chemotaxis concentration-dependently.

Signaling Enzyme Inhibitors Affect Aβ-Induced Migration

Monocytes are incubated with several enzyme blockers. The protein kinase C inhibitor GFX, the tyrosine kinase inhibitor tyrphostin-23, and the phospholipase-3 inhibitor WTN are used first for blocking signaling enzymes; involvement of G proteins is then tested with PTX which is known to induce Gi proteins, and CTX which induces Gs proteins. After washing, chemotaxis experiments toward Aβ (1 pmol/l) and Aβ-PP (1 pmol/l) are performed. Data are expressed as chemotaxis index, which is the ratio between directed and random migration. Mean distance of random migration is 54±3.2 µm.

TABLE 1

| | Chemotaxis Index | |
|---|---|---|
| Treatment | Aβ Mean (+/−SEM) | Aβ-PP Mean (+/−SEM) |
| Medium | 1.786 (0.078) | 1.639 (0.076) |
| GFX (500 nmol/l) | 1.143 (0.08) | 1.098 (0.10) |
| IBMX (10 ng/ml) | 1.234 (0.06) | 1.208 (0.09) |
| Tyrphostin-23 (10 ng/ml) | 1.435 (0.04) | 1.398 (0.07) |
| WTN (10 nmol/l) | 1.023 (0.05) | 1.115 (0.08) |
| CTX (1 nmol/l) | 1.768 (0.10) | 1.790 (0.13) |
| PTX (1 nmol/l) | 1.098 (0.08) | 1.123 (0.06) |

N,N-dimethylsphingosine Inhibits Aβ- and Aβ-PP-Induced Monocyte Migration

Human monocytes are pre-treated with the selective sphingosine kinase inhibitor, DMS, at different concentrations (e.g. 100 fmol/l to 100 nmol/l). fMLP is used as a control attractant. Treatment with DMS inhibits Aβ- and Aβ-PP-induced chemotaxis, whereas fMLP-induced chemotaxis is not affected.

S1P Receptor Agonist Deactivates Migration of Human Monocytes Toward Aβ and Chemokines Monocytes are incubated with DMS, Compound A or medium for 20 min. After washing, chemotaxis experiments toward Aβ [1 pmol/L] are performed. Data are expressed as chemotaxis index, which is the ratio between directed and random migration. Mean distance of random migration is 56±5.6 μm. DMS and a S1P receptor agonist alone inhibit the migration of the cells, whereas co-treatment with both restores the chemotactic effect of Aβ and Aβ-PP. Results with Compound A are as follows:

TABLE 2

| Treatment | Chemotaxis Mean (+/−SEM) |
| --- | --- |
| Medium | 1.825 (0.14) |
| DMS (2 ng/ml) | 1.423 (0.18) |
| Compound A (2 ng/ml) | 1.077 (0.18) |

S1P Receptor mRNA Expression is Regulated by Aβ

After pretreatment with Compound A at various concentrations [20 pg/mL to 20 μg/mL] for 20 min, cells are washed and chemotaxis toward Aβ and Aβ-PP [1 pM] is tested as described above. Data are expressed as chemotaxis index, which is the ratio between directed and undirected migration of cells. After the incubation period, RT-PCR is performed and equal amounts of cDNA are subjected to agarose gel electrophoresis. Induction of S1PR 2 and S1PR 5 mRNA in Aβ-treated cells is observed.

B. Clinical Trial

The trial is carried out employing groups comprising 6 to 10 subjects identified as exhibiting mild to moderate Alzheimer dementia in accordance with parameters defined in DSM-III (Diagnostic and Statistical Manual of Mental Disorders, 3rd edition) and excluding subjects exhibiting severe cardiovascular disease, hypotension, severe endocrine disease, severe liver disease, renal insufficiency. The trial commences with an EEG and psychometric test at time 0. Subjects then receive placebo, or test medication administered as described below, and the EEG and psychometric tests are repeated 60, 120 and 180 minutes subsequent to administration. Psychometric tests employed include:
(i) The Selective Reminding Test/Buschke: "Selective Reminding for Analysis of Memory and Learning", J. Verbal Learning and Verbal Behaviour 12, 543-550 (1973);
(ii) Measurement of Constructional Ability (Muratomo et al.: "Effect of Physiostigmin on Constructional and Memory Tasks in Alzheimer's disease", Arch. Neurol. 36, 501-503 (1973); and
(iii) Memory of Geometric Figures (Benton revised visual retention test).
During the course of the trial, subjects receive either a placebo or a S1P receptor agonist, e.g. Compound A, at dosages of from ca. 0.25 to ca. 10 mg/p.o. administered once or in divided dosages 2 or 3×.
The Following Additional Parameters are Monitored:
  Haematology: R.B.C., HB, HCT, W.B.C., differential counts, sedimentation rate, blood glucose.
  Urine: Albumin, glucose.
  Serum: Alkaline phosphatase, ALT, AST, S-GT, S-bilirubin, S-T4, S-T3, S-TSH, creatinin.
Subjects receiving a S1P receptor agonist, e.g. Compound A, in the above indicated dosages exhibit improved condition as evidenced by EEG results and the results of psychometric tests as compared with subjects receiving placebo.

Daily dosages required in practicing the method of the present invention when S1P receptor agonist is used will vary depending upon, for example, the compound used, the host, the mode of administration and the severity of the condition to be treated. A preferred daily dosage range is about from 0.1 to 100 mg as a single dose or in divided doses. Suitable daily dosages for patients are on the order of from e.g. 0.1 to 50 mg p.o. The S1P receptor agonist may be administered by any conventional route, in particular enterally, e.g. orally, e.g. in the form of tablets, capsules, drink solutions, nasally, pulmonary (by inhalation) or parenterally, e.g. in the form of injectable solutions or suspensions. Suitable unit dosage forms for oral administration comprise from ca. 0.1 to 30 mg, usually 0.25 to 30 mg S1P receptor agonist, e.g. Compound A, together with one or more pharmaceutically acceptable diluents or carriers therefor.

The S1P receptor agonist may be administered by any conventional route, in particular enterally, e.g. orally, for example in the form of solutions for drinking, tablets or capsules or parenterally, for example in the form of injectable solutions or suspensions, or topically. Pharmaceutical compositions comprising a S1P receptor agonist, e.g. a compound of formula I may be manufactured in conventional manner, e.g. as described in EP-A1-627,406 or in EP-A1-1,002,792.

The S1P receptor agonists may be administered as the sole ingredient or together with other drugs useful in the alleviation or treatment of brain degenerative diseases or progressive dementia, e.g. an AMPA receptor agonist, a noortropic agent, a painkiller or an anti-inflammatory agent.

The term "AMPA receptor antagonist" as used herein includes, but is not limited to an quinoxaline-dione aminoalkylphosphonate, e.g. as disclosed in WO 98/17672, or to further compounds such as EGIS 8332 (7-acetyl-5-(4-aminophenyl)-8,9-dihydro-8-methyl-7H-1,3-dioxolo[4,5-h][2,3]benzodiazepine-8-carbonitrile), GYK147261 4-(7-chloro-2-methyl-4H-3,10,10a-triaza-benzo[f]azulen-9-yl)-phenylamine), irampanel (BIIR 561; N,N-dimethyl-2-[2-(3-phenyl-1,2,4-oxadiazol-5-yl)phenoxy]ethanamine), KRP 199 (7-[4-[[[[(4-carboxyphenyl)-amino]carbonyl]oxy]methyl]-1H-imidazol-1-yl]-3,4-dihydro-3-oxo-6-(trifluoromethyl)-2-quinoxalinecarboxylic acid), NS 1209 (2-[[[5-[4-[(dimethylamino)-sulfonyl]phenyl]-1,2,6,7,8,9-hexahydro-8-methyl-2-oxo-3H-pyrrolo[3,2-h]isoquinolin-3-ylidene]amino]oxy]-4-hydroxybutanoic acid monosodium salt, e.g. prepared as described in WO 98/14447), topiramate (TOPAMAX, 2,3:4,5-bis-O-(1-methylethylidene)-beta-D-fructopyranose sulfamate, preparation, e.g. as described in U.S. Pat. No. 535,475) and talampanel (LY-300164, (R)-7-acetyl-5-(4-aminophenyl)-8,9-dihydro-8-methyl-7H-1,3-dioxolo[4,5-h][2,3]benzo-diazepine, preparation, e.g. as described in EP 492485), YM90K (6-imidazol-1-yl-7-nitro-1,4-dihydroquinoxaline-2,3-dione), S-34730 (7-chloro-6-sulfamoyl-2-(1H)-quinolinone-3-phosphonic acid), Zonampanel (YM-872; (7-imidazol-1-yl-6-nitro-2,3-dioxo-3,4-dihydro-2H-quinoxalin-1-yl)-acetic acid), GYKI-52466 (4-(8-methyl-9H-1,3-dioxa-6,7-diaza-cyclohepta[f]inden-5-yl)-phenylamine), ZK-200775 (MPQX, (7-morpholin-4-yl-2,3-dioxo-6-trifluoromethyl-3,4-dihydro-2H-quinoxalin-1-ylmethyl)-phosphonic acid), CP-465022 (3-(2-chlorophenyl)-2-[2-(6-diethylaminomethyl-pyridin-2-yl)-vinyl]-6-fluoro-3H-quinazolin-4-one), SYM-2189 (4-(4-aminophenyl)-6-methoxy-1-methyl-1H-phthalazine-2-carboxylic acid propylamide), SYM-2206 (8-(4-amino-phenyl)-5-methyl-5H-[1,3]dioxolo[4,5-g]phthalazine-6-carboxylic acid propylamide, RPR-117824 ((4-oxo-2-phosphono-5,10-dihydro-4H-imidazo[1,2-a]indeno[1,2-e]pyrazin-9-yl)-acetic acid), LY-293558 (6-[2-(1H-tetrazol-5-yl)-ethyl]-decahydro-isoquinoline-3-carboxylic acid).

The term "nootropics" as used herein includes, but is not limited to nootropical plant extracts, calcium antagonists, cholinesterase inhibitors, dihydroergotoxin, nicergoline, piracetame, purine derivates, pyritinol, vincamine and vinpocetine. The term "nootropical plant extracts" as used herein includes, but is not limited to extracts from Ginkgo leafs. The term "calcium antagonists" as used herein includes, but is not limited to cinnarizine and nimodipine. The term "cholinesterase inhibitors" as used herein includes, but is not limited to donepezil hydrochloride, rivastigmine and galantamine hydrobromide. The term "purine derivates" as used herein includes, but is not limited, to pentifyllin. A painkiller as used herein includes, but is not limited, to ibuprofen. A suitable anti-inflammatory agent is e.g. a NSAIDs, e.g. naproxen.

Extracts from Ginkgo leafs can be administered, e.g., in the form as marketed, e.g. under the trademark Ginkodilat™ according to the information provided by the package insert. Cinnarizine can be administered, e.g., in the form as marketed, e.g. under the trademark Cinnarizin Forte-Ratiopharm™. Nimodipine can be administered, e.g., in the form as marketed, e.g. under the trademark Nimotop™ Donepezil hydrochloride can be administered, e.g., in the form as marketed, e.g. under the trademark Aricept™. Rivastigmine can be prepared as disclosed in U.S. Pat. No. 5,602,176. It can be administered, e.g., in the form as marketed, e.g. under the trademark Exelon™. Galantamine hydrobromide can be administered, e.g., in the form as marketed, e.g. under the trademark Reminyl™ Dihydroergotoxin can be administered, e.g., in the form as marketed, e.g. under the trademark Hydergin™. Nicergoline can be administered, e.g., in the form as marketed, e.g. under the trademark Sermion™ Piracetam can be administered, e.g., in the form as marketed, e.g. under the trademark Cerebroforte™. Pentifyllin can be administered, e.g., in the form as marketed, e.g. under the trademark Cosaldon™. Pyritinol can be administered, e.g., in the form as marketed, e.g. under the trademark Encephabol™. Vinpocetin can be administered, e.g., in the form as marketed, e.g. under the trademark Caviton™.

The structure of the active ingredients identified by code nos., generic or trade names mentioned herein may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active ingredients and, based on these references, likewise enabled to manufacture.

Where the S1P receptor agonists are administered in conjunction with other drugs, dosages of the co-administered compound will of course vary depending on the type of co-drug employed, on the specific drug employed, on the condition to be treated, and so forth. The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

In accordance with the foregoing the present invention provides in a yet further aspect:

5. A pharmaceutical combination comprising a) a first agent which is a S1P receptor agonist, e.g. a compound of formula I, e.g. Compound A, or a pharmaceutically acceptable salt thereof, and b) a co-agent, e.g. a second drug agent as defined above.

6. A method as defined above comprising co-administration, e.g. concomitantly or in sequence, of a therapeutically effective amount of a S1P receptor agonist, e.g. a compound of formula I, e.g. Compound A, or a pharmaceutically acceptable salt thereof, and a second drug substance, e.g. as indicated above.

S1P receptor agonists are well tolerated at dosages required for use in accordance with the present invention. For example, Compound A has an acute $LD_{50}$>10 mg/kg p.o. in rats and monkeys.

---

The invention claimed is:

1. A method of treating a disease or disorder selected from amyloidosis, Alzheimer's disease, Lewy body disease, multi-infarct dementia, and Pick's disease in a subject in need thereof, comprising administering to said subject a therapeutically effective amount of 2-amino-2-[2-(4-octylphenyl)ethyl]propane-1,3-diol in free or pharmaceutically acceptable salt form.

2. A method according to claim 1 further comprising administering, concomitantly or in sequence with the administration of 2-amino-2-[2-(4-octylphenyl)ethyl]propane-1,3-diol in free or pharmaceutically acceptable salt form, a co-agent that is useful in the treatment of brain degenerative diseases or progressive dementia.

3. A method according to claim 1, wherein the hydrochloride salt of 2-amino-2-[2-(4-octylphenyl)ethyl]propane-1,3-diol is administered.

4. A method according to claim 2, wherein the hydrochloride salt of 2-amino-2-[2-(4-octylphenyl)ethyl]propane-1,3-diol is administered.

5. A method according to claim 3, further comprising administering, concomitantly or in sequence with the administration of 2-amino-2-[2-(4-octylphenyl)ethyl]-propane-1,3-diol in free or pharmaceutically acceptable salt form, a co-agent that is useful in the treatment of brain degenerative diseases or progressive dementia.

6. A method according to claim 5, wherein the hydrochloride salt of 2-amino-2-[2-(4-octylphenyl)ethyl]propane-1,3-diol is administered.

* * * * *